(12) United States Patent
Fukaya et al.

(10) Patent No.: US 10,058,451 B2
(45) Date of Patent: Aug. 28, 2018

(54) LACRIMAL DUCT TUBE

(71) Applicant: KANEKA CORPORATION, Osaka-shi, Osaka (JP)

(72) Inventors: Kohei Fukaya, Osaka (JP); Hidekazu Miyauchi, Settsu (JP); Mariko Matsumoto, Settsu (JP); Chihiro Koga, Settsu (JP)

(73) Assignee: KANEKA CORPORATION, Osaka-shi (JP)

( * ) Notice: Subject to any disclaimer, the term of this patent is extended or adjusted under 35 U.S.C. 154(b) by 274 days.

(21) Appl. No.: 14/763,075

(22) PCT Filed: Jan. 21, 2014

(86) PCT No.: PCT/JP2014/051052
§ 371 (c)(1),
(2) Date: Jul. 23, 2015

(87) PCT Pub. No.: WO2014/115700
PCT Pub. Date: Jul. 31, 2014

(65) Prior Publication Data
US 2015/0351962 A1 Dec. 10, 2015

(30) Foreign Application Priority Data
Jan. 24, 2013 (JP) ................................ 2013-011541

(51) Int. Cl.
*A61F 9/007* (2006.01)
(52) U.S. Cl.
CPC ............... *A61F 9/00772* (2013.01)
(58) Field of Classification Search
CPC ............. A61M 27/002; A61M 25/0067; A61F 9/00772
See application file for complete search history.

(56) References Cited

U.S. PATENT DOCUMENTS 4,305,395 A 12/1981 Martinez
4,658,816 A 4/1987 Ector, Jr.
(Continued)

FOREIGN PATENT DOCUMENTS

JP 10-33584 A 2/1998
JP 2001-327525 A 11/2001
(Continued)

OTHER PUBLICATIONS

International Search Report, issued in PCT/JP2014/051052, dated Mar. 11, 2014.

*Primary Examiner* — Leslie Deak
(74) *Attorney, Agent, or Firm* — Birch, Stewart, Kolasch & Birch, LLP

(57) ABSTRACT

A lacrimal duct tube including: a pair of tubular members each of which has an terminal end opening at one end; and a central member that connects other ends of the tubular members, at least one of the tubular members includes: a cylindrical part extended from the terminal end opening to the central member side and has an opening for bar-like operative instrument at an end portion at the central member side; and an arc-shaped part that is extended from the end portion of the cylindrical part at the central member side further to the central member side and has an almost arc-shaped wall portion on a cross section orthogonal to a longitudinal side of the tubular member, and the almost arc-shaped wall portion is formed at the arc-shaped part continuously over a length of ⅓ or more and 9/10 or less of an entire length of the tubular member.

13 Claims, 10 Drawing Sheets

(56) References Cited

U.S. PATENT DOCUMENTS

| | | |
|---|---|---|
| 2002/0107579 A1 | 8/2002 | Makino |
| 2005/0125072 A1* | 6/2005 | Kolb .................... A61M 27/008 623/23.7 |
| 2009/0281621 A1* | 11/2009 | Becker ................ A61F 9/00772 623/10 |
| 2012/0215153 A1 | 8/2012 | Fukaya et al. |

FOREIGN PATENT DOCUMENTS

| | | |
|---|---|---|
| JP | 2006-181054 A | 7/2006 |
| JP | 2006-312034 A | 11/2006 |
| JP | 2007-512899 A | 5/2007 |
| JP | 2010-213957 A | 9/2010 |
| WO | WO 01/67995 A1 | 9/2001 |
| WO | WO 2005/060868 A1 | 7/2005 |
| WO | WO 2011/049198 A1 | 4/2011 |

\* cited by examiner

[Fig. 1]
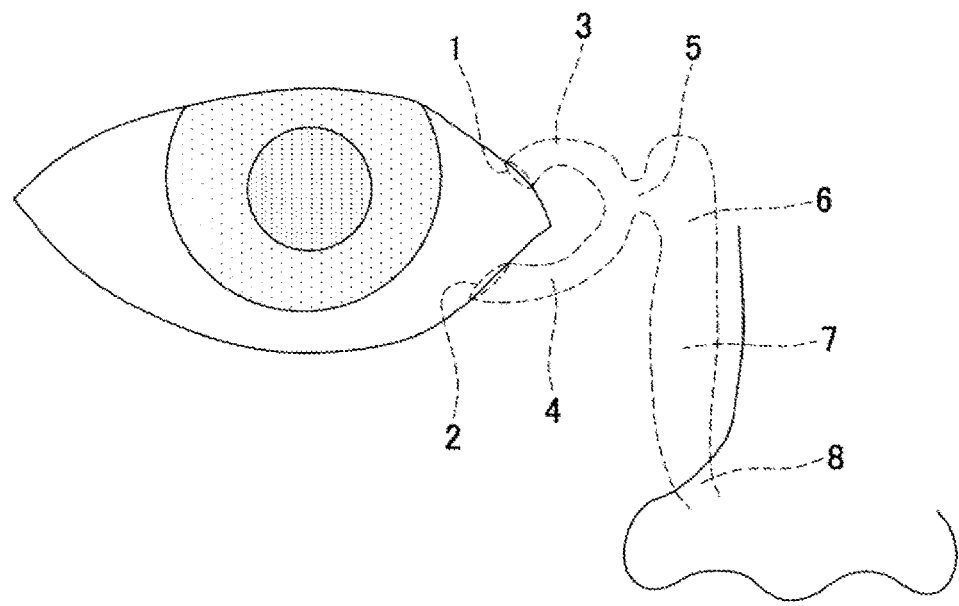
[Fig. 2]
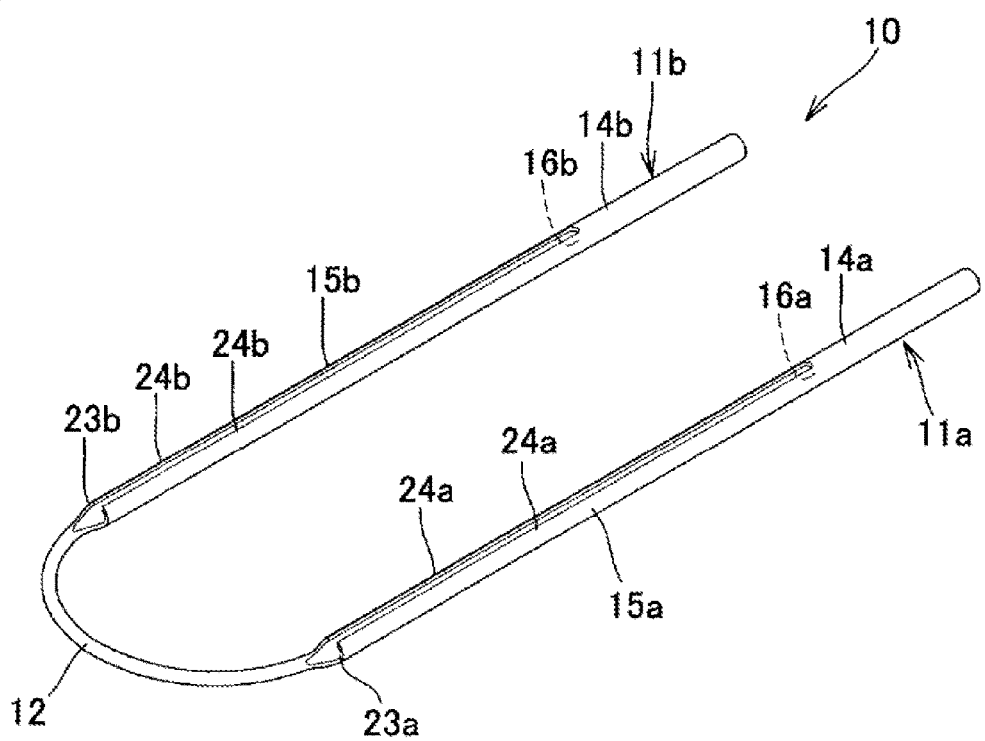

[Fig. 3]
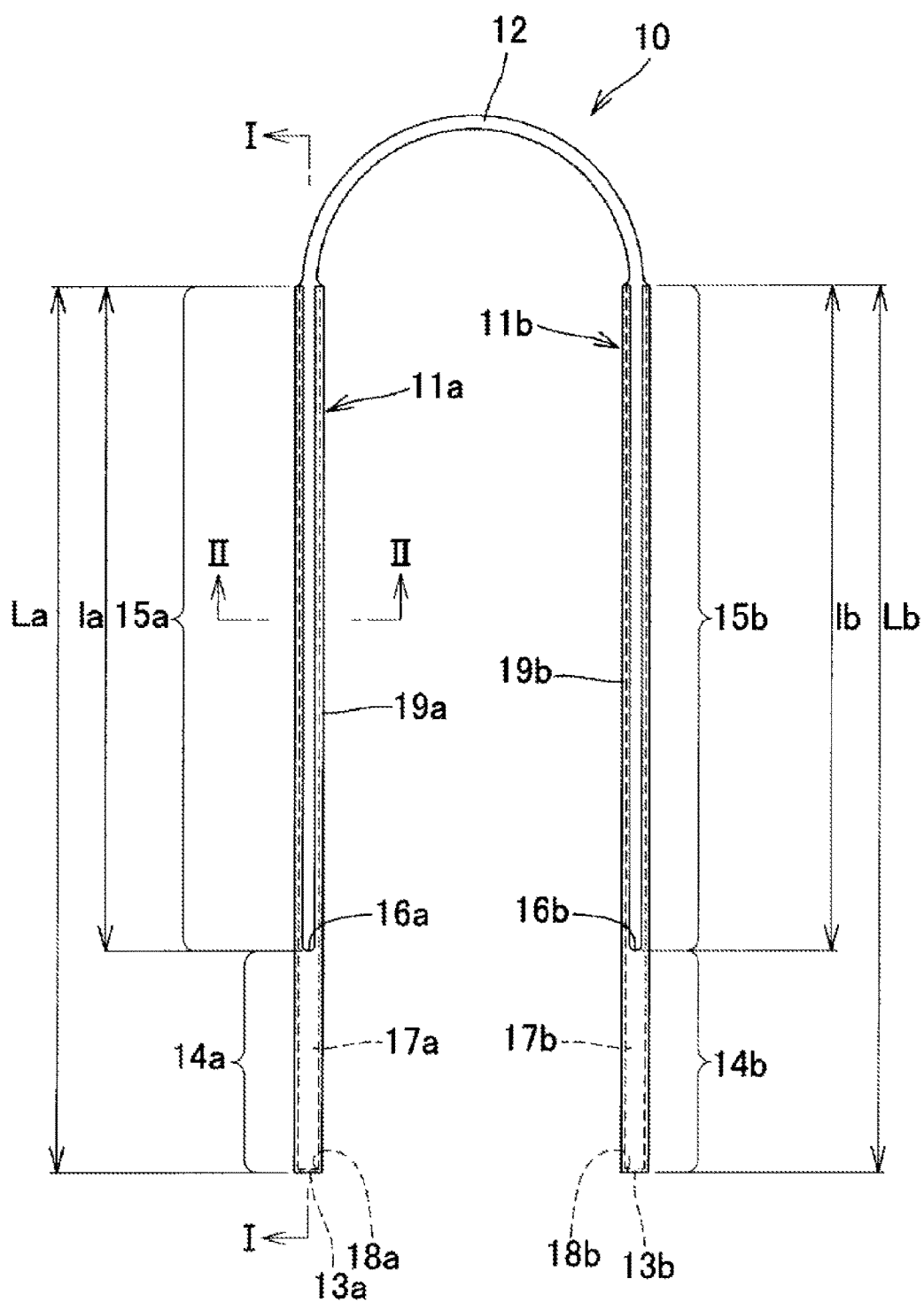

[Fig. 4]
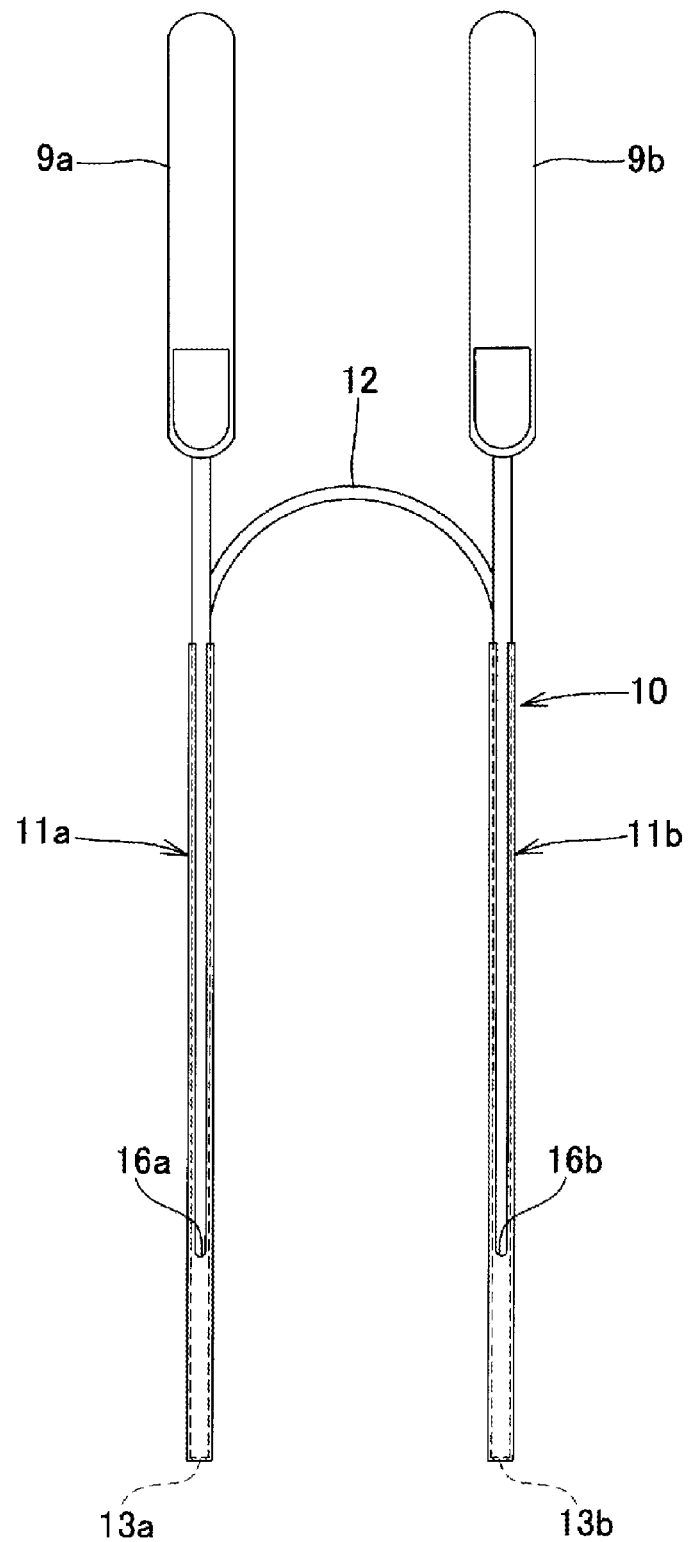

[Fig. 5]
(a)
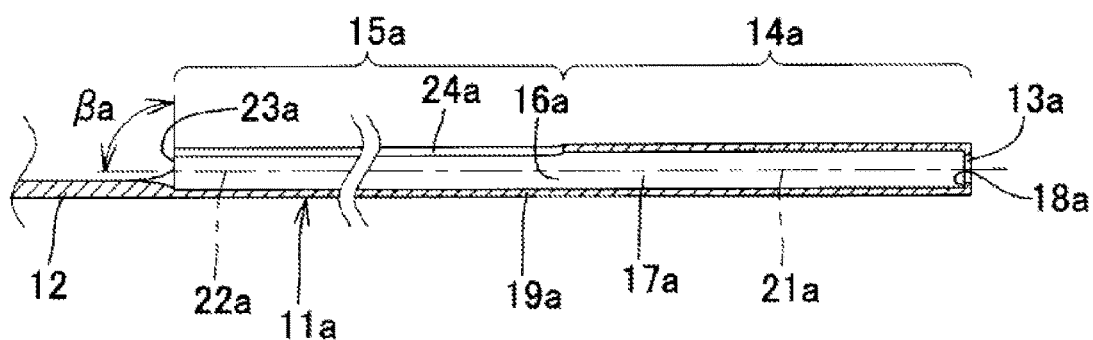
(b)
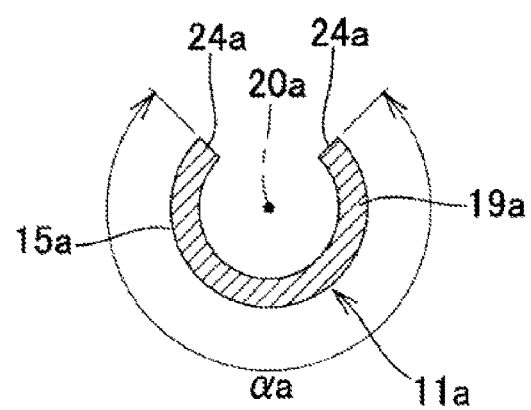

[Fig. 6]
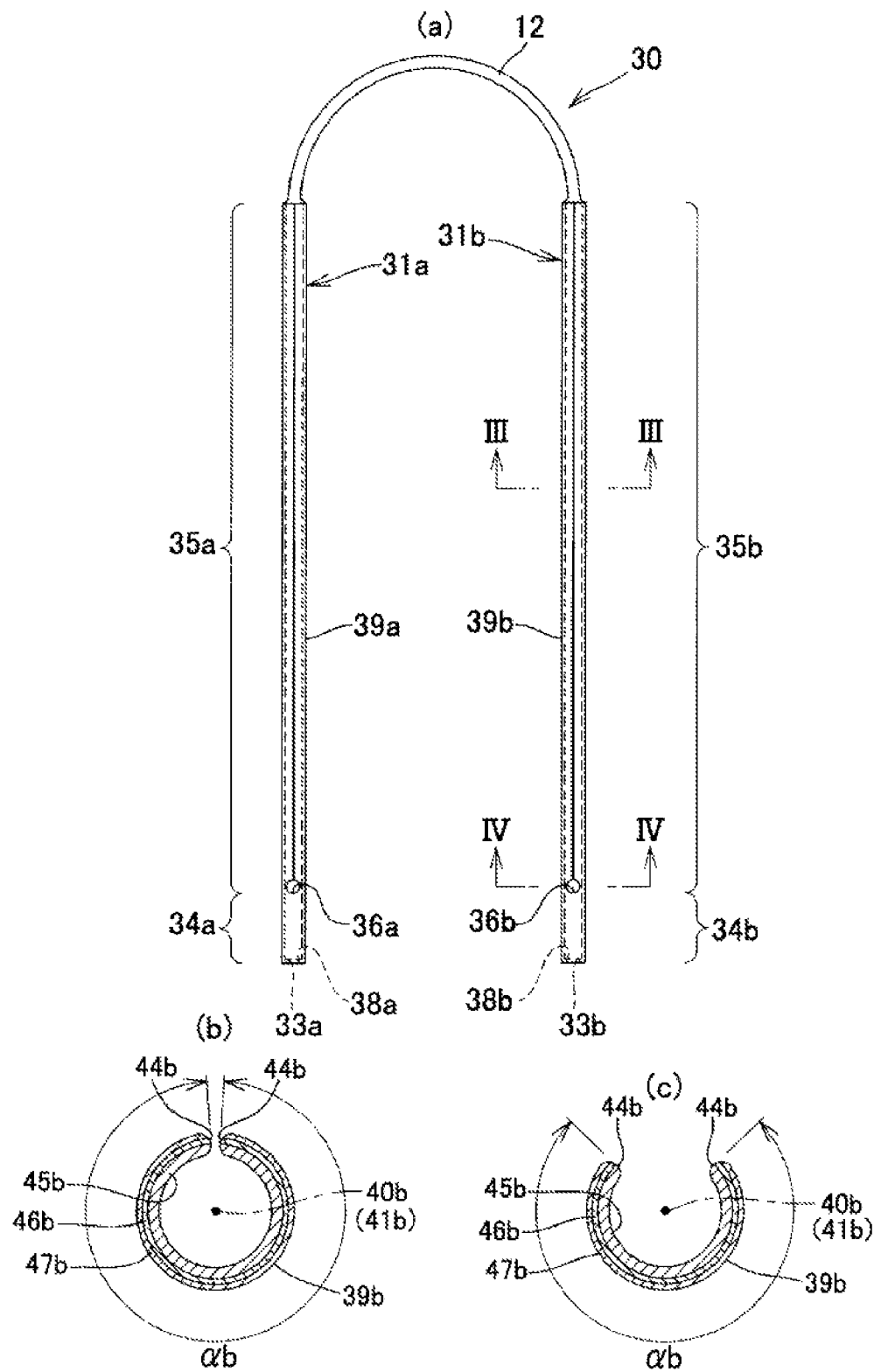

[Fig. 7]
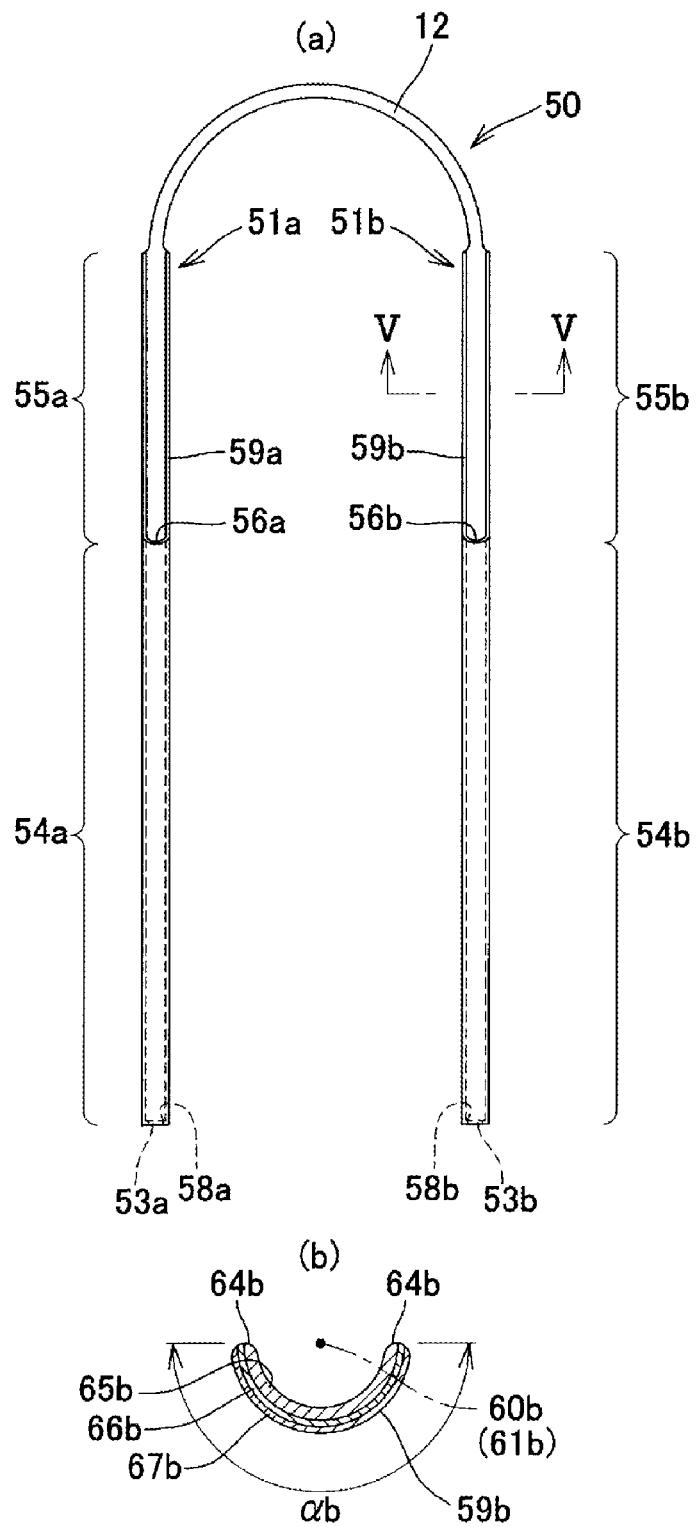

[Fig. 8]
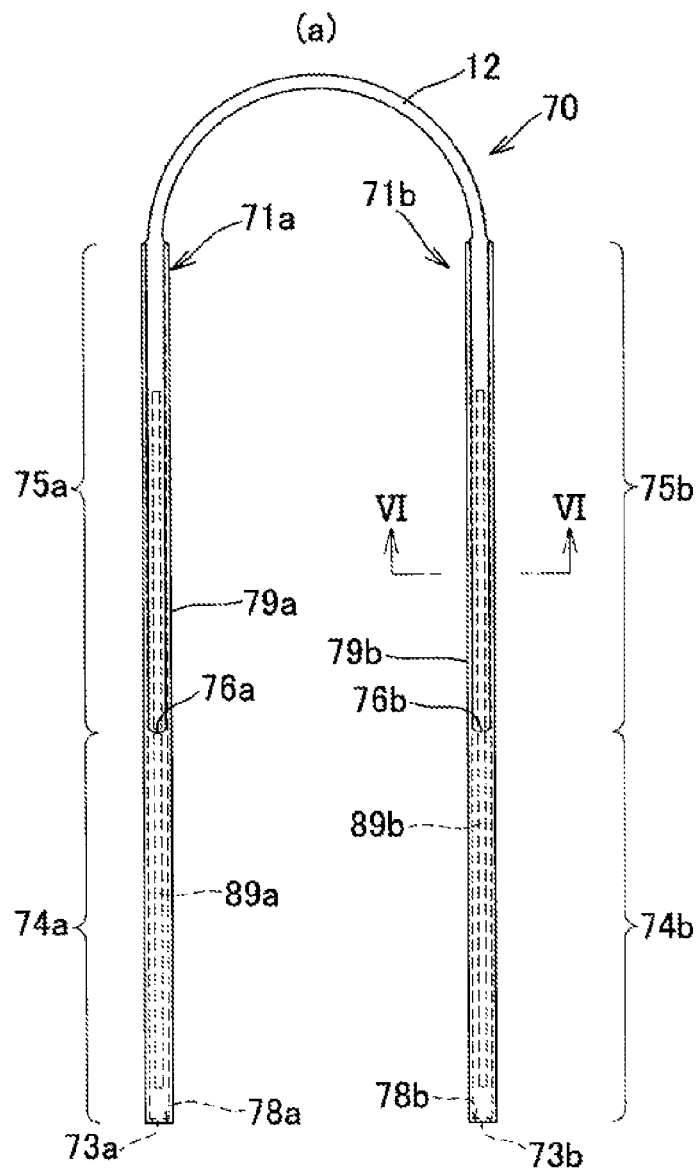
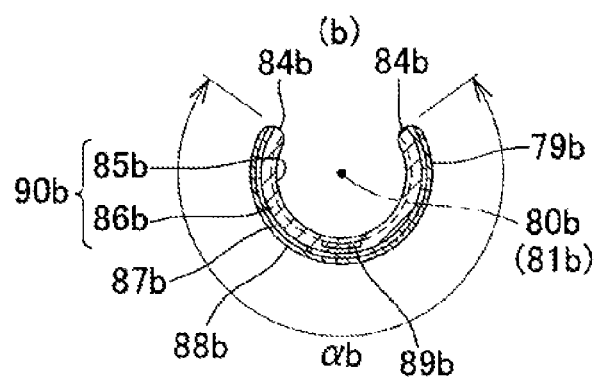

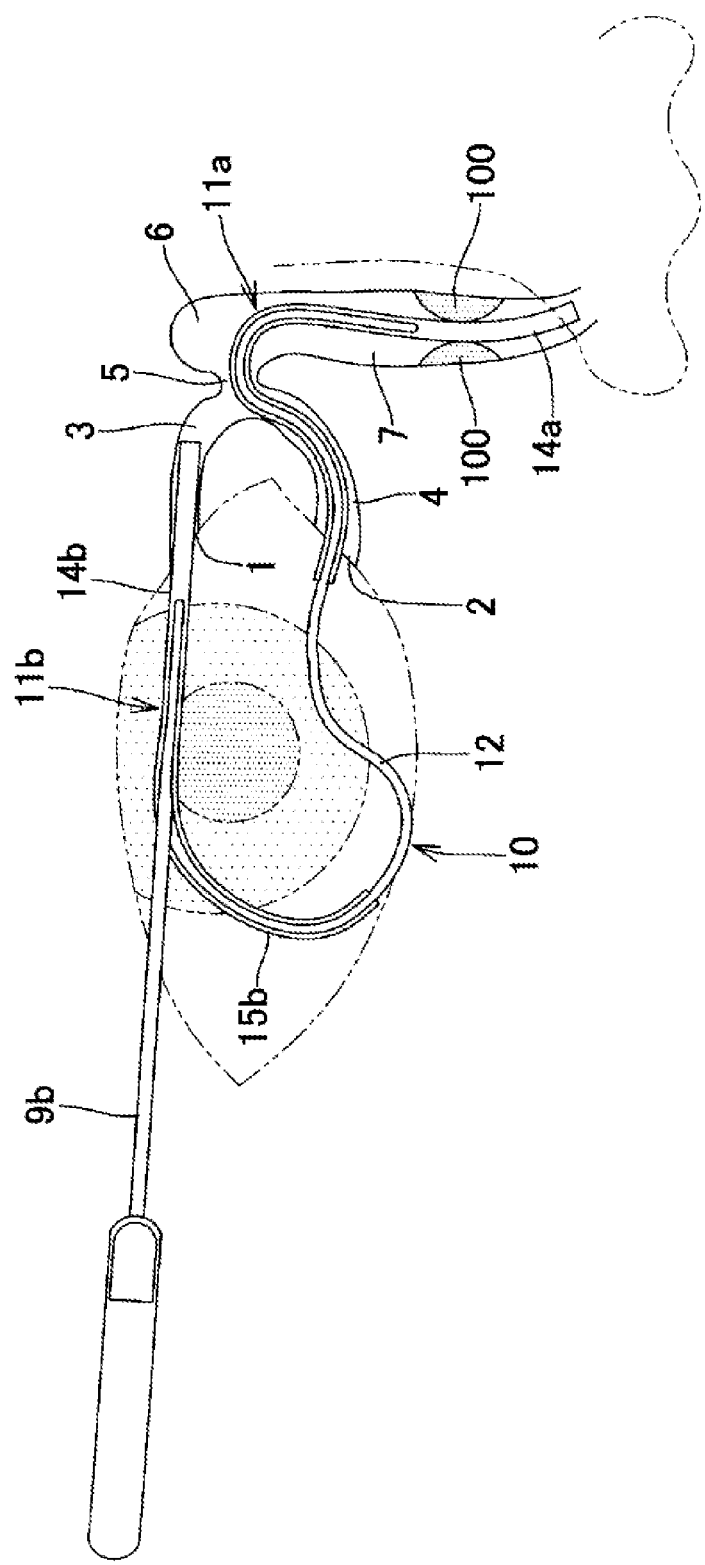
[Fig. 9]

[Fig. 10]
(a)
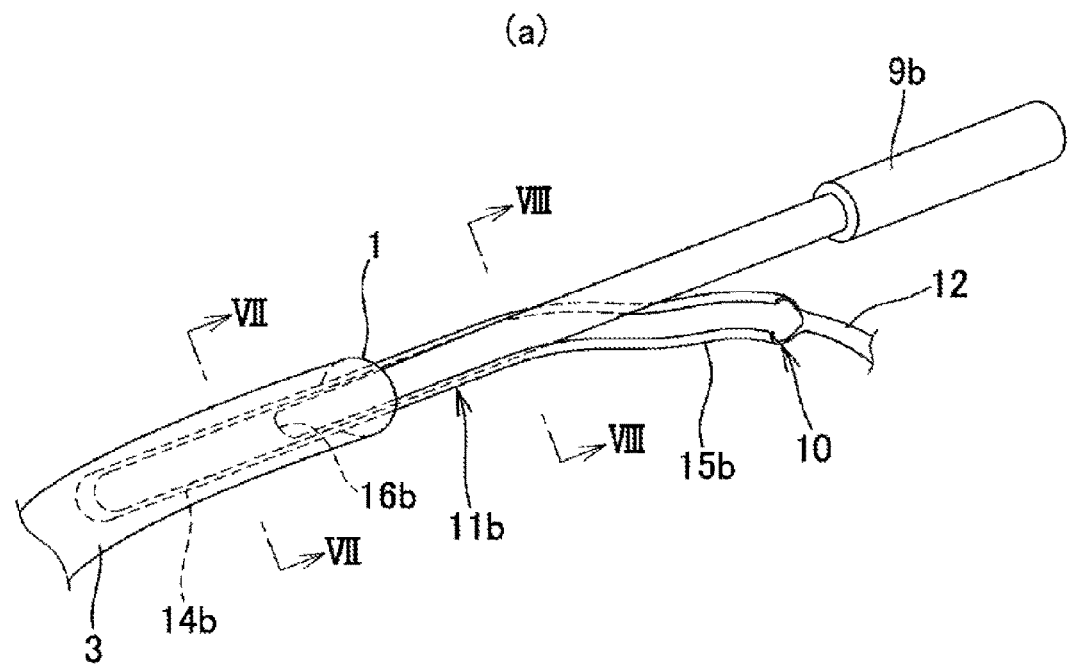
(b)
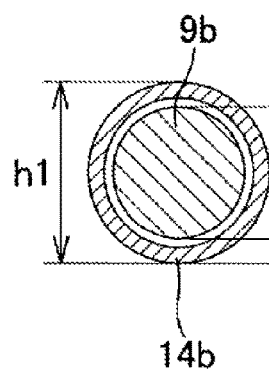
(c)
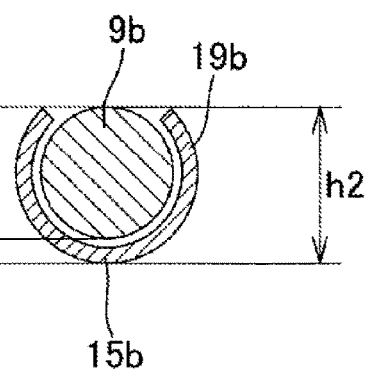

[Fig. 11]
(a)
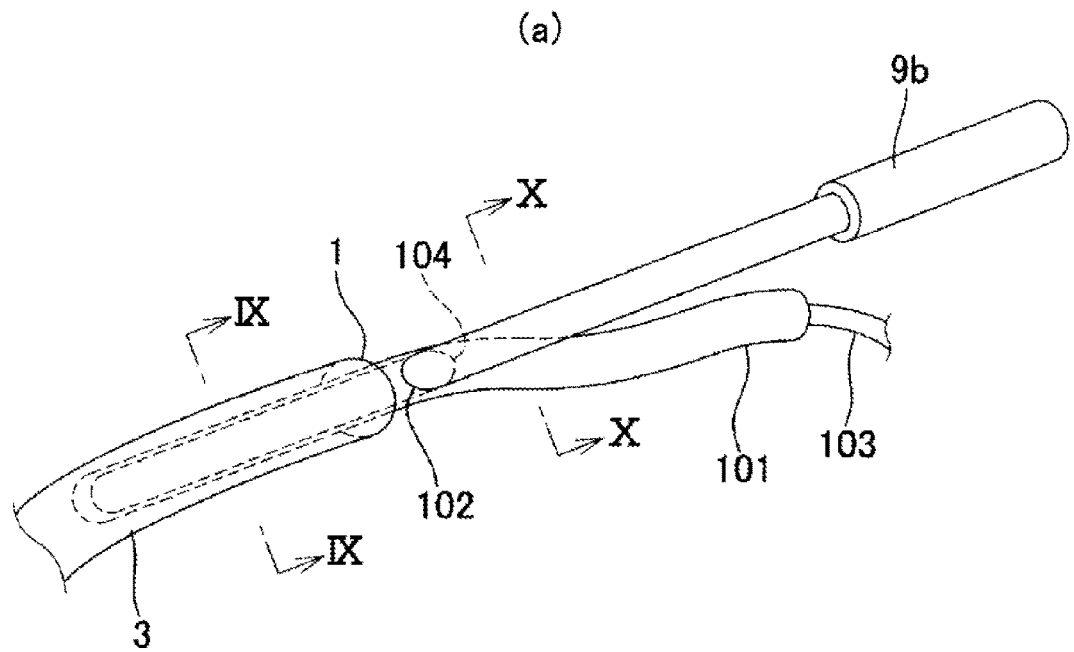
(b)    (c)
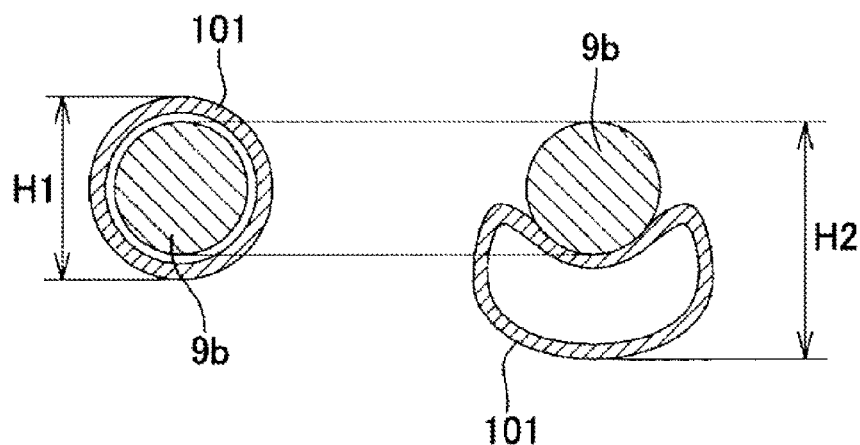

LACRIMAL DUCT TUBE

TECHNICAL FIELD

The present invention relates to a lacrimal duct tube for use in treatment of lacrimal duct obstruction.

BACKGROUND ART

Treatment methods for lacrimal duct obstruction resulting in epiphora include: (i) probing by a lacrimal duct bougie; (ii) placement of a lacrimal duct tube; (iii) dacryocystorhinostomy (DCR); (iv) lacrimal canaliculization; (v) nasolacrimal duct plastic surgery; (vi) lacrimal caruncle moving surgery, and the like.

The probing by a lacrimal duct bougie in (i) is intended to insert a narrow tube called bougie into a lacrimal duct to open an obstructed site and reconstruct a flow path for a lacrimal fluid. This method is conducted as a first treatment in many cases due to its ease of execution and minimal invasiveness. The treatments (iii) dacryocystorhinostomy (DCR), (iv) lacrimal canaliculization, (v) nasolacrimal duct plastic surgery, and (vi) lacrimal caruncle moving surgery are highly effective but relatively invasive because of the need for creation of incisions in a patient's face or drilling holes in bones, and thus are conducted as a last resort.

Lacrimal duct tube for use in the treatment method (ii) is, after the probing by a lacrimal duct bougie (i), placed for maintaining of a flow path and reconstruction of tissues. The placement of a lacrimal duct tube (ii) is easy, less invasive, and highly effective as compared to the foregoing treatment methods (iii) to (vi), and thus is widely performed all over the world. Among such instruments, there is widely available a lacrimal duct tube in which a central part of the tube is formed by a narrow and soft tube or rod and both sides of the tube are formed by hard and thick tubes, as disclosed in Patent Document 1 (for example, refer to FIG. 1).

The lacrimal duct tube includes a tube and a pair of bougies that is inserted from incisions at both sides of the tube, and the bougies are operated to guide the tube into a lacrimal duct and place the tube there. As shown in FIG. 2 of Patent Document 1, a lacrimal duct is formed by lacrimal puncta (21 and 22), lacrimal canaliculi (23 and 24), a lacrimal sac (26), a nasolacrimal duct (27), and others. The lacrimal duct tube is inserted into the lacrimal duct.

However, to insert the lacrimal duct tube, it is necessary to fumble for intra-lacrimal duct operations. The bougies are blindly operated and thus may break through the tube or make a hole at a site other than in the normal lacrimal duct (creating a temporary path), which results in poor therapeutic outcomes. Accordingly, to solve the foregoing problem, the inventor of the present invention has suggested in the past a lacrimal duct intubation instrument in which openings are formed at the tips of a lacrimal duct tube, reinforcement bodies are arranged and held in the vicinities of the openings, and the positions of the reinforcement bodies are adjusted within predetermined distances from the openings (refer to Patent Document 1).

In the recent year's field of lacrimal duct obstruction treatment, surgeries have been newly conducted based on a sheath guided endoscopic probing. At these surgeries, a sheath as an outer casing made of Teflon (registered trademark) or polyurethane covering a lacrimal endoscope was advanced ahead of the lacrimal endoscope in the lacrimal duct to observe from behind that the tip of the sheath opens the obstructed site in the lacrimal duct. In addition, exact tube insertion is allowed by using the sheath as a guide for tube insertion. This technique will be specifically described below. First, the sheath attached to the lacrimal endoscope is inserted into an obstructed site in the lacrimal duct and passed through the obstructed site, and then the lacrimal endoscope is removed. Next, a lacrimal duct tube is connected to the sheath, and the sheath is pulled from the side opposite to the connection side of the lacrimal duct tube to let the lacrimal duct tube pass through the lacrimal duct. Then, the sheath is removed to place the lacrimal duct tube in the lacrimal duct.

However, according to the foregoing surgery, there is the need for a step of connecting the sheath inserted into the patient's lacrimal duct to the lacrimal duct tube. In addition, occurrence of the disconnection may result in an unsuccessful surgery. Thus, there is room for improvement in the method to secure manipulation of the instruments and reduce complexity of the operation.

Meanwhile, instead of using the sheath, a lacrimal endoscope may be inserted into a lacrimal duct tube. For example, as lacrimal duct tubes usable with a lacrimal endoscope therein, there are known: 1) a lacrimal duct intubation instrument as described in Patent Document 1 that has openings at the terminal ends of a lacrimal duct tube and reinforcement bodies arranged and held in the vicinities of the openings, the positions of the reinforcement bodies being adjusted to be at predetermined distances from the openings; and 2) a lacrimal duct treatment tool including a lacrimal duct placement main body that has an outer diameter allowing insertion into the lacrimal duct and is formed from flexible material and sheath parts composed of flexible cylindrical bodies that are provided at the lower ends of the lacrimal duct placement main body and are formed from harder material than that for the lacrimal duct placement main body (refer to Patent Document 2).

However, the lacrimal duct intubation instrument described in Patent Document 1 has a complicated lacrimal duct tube structure, and the reinforcement bodies cannot be significantly smaller in diameter, and the terminal ends of the tube are difficult to harden and thus tend to be slightly weak in pressing force (pushability). In addition, when performing operations with the lacrimal duct tube, it is necessary to carefully operate the endoscope inserted into the tube because friction between the lacrimal duct tube and the endoscope becomes large depending on the material for the lacrimal duct tube. Further, the lacrimal duct intubation instrument described in Patent Document 1 (refer to FIGS. 1 and 3(a) in particular) has insertion portions at the cylindrical parts for insertion of a bougie or a lacrimal endoscope. The insertion portions are slits or tiny holes that are small enough for insertion of a bougie or a lacrimal endoscope. In the case where the insertion portions have such a structure, when, while one cylindrical part is inserted from one lacrimal punctum into the lacrimal duct and held at a predetermined position, an attempt is made to insert the other cylindrical part from the other lacrimal punctum into the lacrimal duct, it may be difficult to insert the other cylindrical part into the other lacrimal punctum. This is because the small insertion portions are provided near the centers of the integral tubes, the bougie or the lacrimal endoscope is of low flexibility, and the like.

The lacrimal duct treatment tool described in Patent Document 2 has also small through holes for insertion of a lacrimal endoscope camera in the sheath parts near the lacrimal duct placement main body. The lacrimal duct treatment tool is entirely long, and even when one sheath part is inserted from one lacrimal punctum into the lacrimal duct and held at its position, the other sheath part can be inserted from the other lacrimal punctum into the lacrimal duct. However, in the case of using the lacrimal duct treatment tool, it is necessary to separate the lacrimal duct treatment tool main body and the sheath parts after placement of the tool in the lacrimal duct, which results in complexity in performing surgeries.

In the conventional lacrimal duct tube as described in Patent Document 1 or 2, the small openings (corresponding to the insertion portions described in Patent Document 1 or the through holes described in Patent Document 2) for insertion of bar-like operative instruments such as lacrimal endoscopes are provided at the side walls of the cylindrical parts or the sheath parts, and a bar-like operative instrument is placed on the outside of the lacrimal duct tube on the central member side (the central part described in Patent Document 1 or the component with reference sign 3 illustrated in FIG. 1 of Patent Document 2). In this case, as illustrated in FIG. 11(*a*), for example, when a conventional lacrimal duct tube 101 is inserted into a lacrimal duct such as an upper lacrimal canaliculus 3 from an upper lacrimal punctum 1, the total width of the lacrimal duct tube 101 and a bar-like operative instrument 9*b* is equal to a width H1 of the lacrimal duct tube 101 at the side into which the bar-like operative instrument 9*b* is inserted (refer to FIG. 11(*b*)). However, at the side of the lacrimal duct tube 101 nearer to a central member 103 across an opening 102, the bar-like operative instrument 9*b* and the slightly deformed lacrimal duct tube 101 overlap each other, and the total width of the two is a width H2 (refer to FIG. 11(*c*)), which is larger than the width H1. Accordingly, it is difficult to insert the lacrimal duct tube 101 into the lacrimal duct beyond the opening 102, which becomes a larger burden on the patient. In addition, at the side of the lacrimal duct tube 101 nearer to the central member 103 across the opening 102, the bar-like operative instrument 9*b* comes into contact with edge 104 of the opening 102 in the lacrimal duct tube 101 at the central member 103 side, which interferes with longitudinal movement of the bar-like operative instrument 9*b*, thereby making the operation hard to perform.

CITATION LIST

Patent Literatures

Patent Document 1: International Publication WO 2011/049198
Patent Document 1: JP-A No. 2010-213957

SUMMARY OF INVENTION

Technical Problem

In light of the foregoing circumstances, an object of the present invention is to provide a lacrimal duct tube that is favorably used in treatment of lacrimal duct obstruction using a lacrimal endoscope, specifically, a lacrimal duct tube that can be placed in a lacrimal duct without having to cut the tube after insertion and makes it possible to, when one tube member is inserted from one lacrimal punctum into the lacrimal duct and held at the inserted position, use a bar-like operative instrument such as a bougie or a lacrimal endoscope to insert the other tube member from the other lacrimal punctum into the lacrimal duct in an easy manner.

Solution to Problem

The inventors have earnestly conducted studies with the aim of solving the foregoing problems. As a result, the inventors have revealed that the foregoing problems could be solved by configuring a lacrimal duct tube such that at least one of tubular members constituting a lacrimal duct tube includes a cylindrical part and an arc-shaped part with an almost arc-shaped wall portion at a cross section orthogonal to a longitudinal side of the tubular member, and the almost arc-shaped wall portion is continuously formed over a predetermined length, thereby completing the present invention.

Specifically, the gist of the present invention is as follows:

[1] A lacrimal duct tube slidable along a bar-like operative instrument, including:
a pair of tubular members each of which has an terminal end opening at one end; and
a central member that connects other ends of the tubular members, wherein
at least one of the tubular members includes: a cylindrical part that is extended from the terminal end opening to the central member side and has an opening for bar-like operative instrument at an end portion at the central member side; and an arc-shaped part that is extended from the end portion of the cylindrical part at the central member side further to the central member side and has an almost arc-shaped wall portion on a cross section orthogonal to a longitudinal side of the tubular member, and
the almost arc-shaped wall portion is formed at the arc-shaped part continuously over a length of ⅓ or more and 9/10 or less of an entire length of the tubular member.

[2] The lacrimal duct tube according to [1], wherein the almost arc-shaped wall portion is formed over an entire longitudinal length of the arc-shaped part.

[3] The lacrimal duct tube according to [1] or [2], wherein a longitudinal central axis of the cylindrical part and a longitudinal central axis of the arc-shaped part are arranged coaxially, and the shortest distance between the central axis and the cylindrical part and the shortest distance between the central axis and the arc-shaped part are equal.

[4] The lacrimal duct tube according to any of [1] to [3], wherein the almost arc-shaped wall portion is continuously arranged such that a central angle with reference to a central point on the cross section orthogonal to the longitudinal side of the arc-shaped part is 180 degrees or more.

[5] The lacrimal duct tube according to any of [1] to [4], wherein the almost arc-shaped wall portion has a portion in which the central angle with reference to the central point on the cross section orthogonal to the longitudinal side of the arc-shaped part is smaller at the opening for bar-like operative instrument side along the longitudinal side of the arc-shaped part.

[6] The lacrimal duct tube according to any of [1] to [5], wherein the cylindrical part is circular cylindrical in shape, and the almost arc-shaped wall portion is a circular arc-shaped wall portion.

[7] The lacrimal duct tube according to any of [1] to [6], wherein the opening for bar-like operative instrument is formed at a position of ⅔ or less of the entire length of the tubular member from the terminal end opening.

[8] The lacrimal duct tube according to any of [1] to [7], wherein the almost arc-shaped wall portion is rounded at both end portions of the cross section orthogonal to the longitudinal side of the tubular member.

[9] The lacrimal duct tube according to any of [1] to [8], wherein the terminal end of the arc-shaped part at the central member side has an end portion orthogonal to the longitudinal side of the arc-shaped part.

[10] The lacrimal duct tube according to any of [1] to [9], wherein the tubular member is composed of a plurality of materials different in Shore hardness, and the material for a portion of the tubular member sliding over the bar-like operative instrument is highest in Shore hardness.

[11] The lacrimal duct tube according to [10], wherein the material for the portion sliding over the bar-like operative instrument is an olefin resin.

[12] The lacrimal duct tube according to [10] or [11], wherein the tubular member has a multilayer structure, and, of the multilayer structure, a layer constituting the portion sliding over the bar-like operative instrument is thickest.

[13] The lacrimal duct tube according to any of [1] to [12], wherein a reinforcement member is arranged from a portion of the arc-shaped part in the vicinity of the central member to a portion continued between the arc-shaped part and the cylindrical part.

[14] The lacrimal duct tube according to [13], wherein the reinforcement member is a stainless steel or a shape-memory alloy.

Advantageous Effects of Invention

According to the lacrimal duct tube in the present invention, at least one of the tubular members includes the cylindrical part to allow a bar-like operative instrument such as a bougie or a lacrimal endoscope to be reliably held in the lacrimal duct tube. The tubular member also includes the arc-shaped part that can be bent while the bar-like operative instrument is inserted into the cylindrical part. Accordingly, the arc-shaped part having a specific structure is extended from the end portion of the cylindrical part. Even when the tubular member is short to the degree that does not need to be cut after placement, it is possible to, after inserting one of the tubular members from one lacrimal punctum into the lacrimal duct and keeping it at that position, use a bar-like operative instrument such as a bougie or a lacrimal endoscope to easily insert the other tubular member from the other lacrimal punctum into the lacrimal duct.

In addition, when the almost arc-shaped wall portion is formed over the entire longitudinal length of the arc-shaped part, the operator can hold the end portion of the arc-shaped part at the central member side to slide the tubular member along the bar-like operative instrument. Accordingly, when a lacrimal endoscope is used as a bar-like operative instrument, even if the tubular member is short, it is possible to move the cylindrical part of the tubular member ahead of the lacrimal endoscope and slide the tubular member along the lacrimal endoscope to easily perform an operation of opening an obstructed site while suppressing a load on the patient.

BRIEF DESCRIPTION OF THE DRAWINGS

FIG. 1 is an illustrative diagram of an anatomical structure of a lacrimal duct;

FIG. 2 is a schematic perspective view of one embodiment of a lacrimal duct tube according to the present invention;

FIG. 3 is a schematic plane view of the lacrimal duct tube illustrated in FIG. 2;

FIG. 4 is a schematic plane view of the lacrimal duct tube in FIG. 2 into which a bar-like operative instrument is inserted;

FIG. 5(a) is a cross-sectional view of FIG. 3 taken along direction I-I, and FIG. 5(b) is a cross-sectional view of FIG. 3 taken along direction II-II;

FIG. 6(a) is a schematic plane view of another embodiment of the lacrimal duct tube according to the present invention, FIG. 6(b) is a cross-sectional view of FIG. 6(a) taken along direction III-III, and FIG. 6(c) is a cross-sectional view of FIG. 6(a) taken along direction IV-IV;

FIG. 7(a) is a schematic plane view of another embodiment of the lacrimal duct tube according to the present invention, and FIG. 7(b) is a cross-sectional view of FIG. 7(a) taken along direction V-V;

FIG. 8(a) is a schematic plane view of another embodiment of the lacrimal duct tube according to the present invention, and FIG. 8(b) is a cross-sectional view of FIG. 8(a) taken along direction VI-VI;

FIG. 9 is an illustrative diagram of a method for using a lacrimal duct tube according to the present invention;

FIG. 10(a) is a schematic perspective view of the lacrimal duct tube according to the present invention that is being inserted into the lacrimal duct, FIG. 10(b) is a schematic cross-sectional view of the lacrimal duct tube in FIG. 10(a) taken along direction VII-VII, and FIG. 10(c) is a schematic cross-sectional view of the lacrimal duct tube in FIG. 10(a) taken along direction VIII-VIII.

FIG. 11 (a) is a schematic perspective view of a conventional lacrimal duct tube that is being inserted into the lacrimal duct, FIG. 11(b) is a schematic cross-sectional view of the lacrimal duct tube in FIG. 11(a) taken along direction IX-IX, and FIG. 11(c) is a schematic cross-sectional view of the lacrimal duct tube in FIG. 11(a) taken along direction X-X.

DESCRIPTION OF EMBODIMENTS

A plurality of embodiments of a lacrimal duct tube according to the present invention will be described below with reference to the accompanying drawings. However, the present invention is not limited to these embodiments.

FIG. 1 illustrates schematically an anatomical structure of a lacrimal duct.

Lacrimal duct referred to in the present invention is a duct (ocular adnexa) composed of upper/lower lacrimal puncta (1/2), upper/lower lacrimal canaliculi (3/4), a common canaliculus (5), a lacrimal sac (6), a nasolacrimal duct (7), a nasal tract (not shown), and Hasner's valve (not shown), as illustrated in FIG. 1, which is configured to guide a lacrimal fluid produced by a lacrimal gland (not shown) from an eye surface to an inferior nasal meatus (8). In addition, a duct extending from the upper lacrimal punctum (1) through the upper lacrimal canaliculus (3), and the common canaliculus (5) to the inferior nasal meatus (8) is referred to as an upper lacrimal duct, and a duct extending from the lower lacrimal punctum (2) through the lower lacrimal canaliculus (4), and the common canaliculus (5) to the inferior nasal meatus (8) is referred to as a lower lacrimal duct.

In addition, the lacrimal duct tube according to the present invention is inserted into and placed in the lacrimal duct to open an obstructed site.

FIG. 2 is a schematic perspective view of one embodiment of a lacrimal duct tube according to the present invention. FIG. 3 is a plane view of the embodiment illustrated in FIG. 2. FIG. 5(a) is a schematic cross-sectional view of FIG. 3 taken along direction I-I, and FIG. 5(b) is a schematic cross-sectional view of FIG. 3 taken along direction II-II. FIG. 4 is a plane view of the embodiment in FIG. 2 into which bar-like operative instruments 9a and 9b are inserted. A lacrimal duct tube 10 in this embodiment includes a pair of tubular members 11a and 11b and a central member 12 connecting the tubular member 11a and the tubular member 11b. In this embodiment, the paired tubular members 11a and 11b are the same in structure. However, they may be different in structure. When they are different in structure, at least one of them needs to include the predetermined cylindrical part and arc-shaped part. The other tubular member may be structured in any conventionally known manner or may have a cylindrical structure opened at both terminal ends thereof, as far as it does not need to be cut after being inserted into the lacrimal duct.

The paired tubular members 11a and 11b have terminal end openings 13a and 13b at one each end. Providing the terminal end openings allows the operator to, when lacrimal endoscopes are used as bar-like operative instruments, guide the lacrimal duct tube into a desired site of the lacrimal duct while checking the inside of the lacrimal duct from the terminal end openings by the use of the lacrimal duct endoscopes.

In this embodiment, the paired tubular members 11a and 11b include cylindrical parts 14a and 14b and arc-shaped parts 15a and 15b.

The cylindrical parts 14a and 14b have luminal parts 17a and 17b that are formed in a circular cylindrical shape and communicate from the terminal end openings 13a and 13b at the one each end to openings 16a and 16b for bar-like operative instrument at end portions on the central member 12 side for insertion of a bar-like operative instrument. In this embodiment, the cylindrical parts 14a and 14b are circular cylindrical in shape, but may have any other structure. For example, the cylindrical parts may be each modified in various manners such that the inside of the cylindrical part (for insertion of a bar-like operative instrument) constitutes a circular cylindrical inner wall surface and the outside of the cylindrical part (for contact with the lacrimal duct) constitutes an oval outer wall surface. Forming the cylindrical parts in a circular cylindrical shape makes it easy to provide the cylindrical parts with desired strength and flexibility while suppressing increase in thickness of the wall portions.

In the present invention, the cylindrical parts may have engagement portions to be engaged with the tip ends of bar-like operative instruments on the inner wall surfaces of the terminal end openings and their neighborhoods. Specifically, the engagement portions of the cylindrical parts constitute sections of the luminal parts with the smallest width so as to be smaller than the largest width of the tip ends of the bar-like operative instruments. In the case of forming the engagement portions, the engagement portions serve as stoppers for the bar-like operative instruments inserted into the cylindrical parts. This makes it possible to, when the lacrimal duct tube is inserted into the lacrimal duct and is passed through an obstructed site, prevent the bar-like operative instruments from projecting from the terminal end openings of the tubular members. In addition, since the lacrimal endoscopes can be arranged in the vicinities of the terminal end openings of the tubular members, it is possible to provide sufficient viewing fields of the endoscopes from the terminal end openings. Further, by inserting the bar-like operative instruments into the lacrimal duct tube, it is possible to improve the lacrimal duct tube in passage (breaking) through a lesion. In addition, while the lacrimal endoscopes are used, it is possible to allow the operator to surely understand the status of the path through which the tube is passed, and avoid the tube from forming a temporary path and causing damage and bleeding to mucous membranes and the like.

Each of the engagement portions can be formed by decreasing the inner diameter of the cylindrical part in the vicinity of the terminal end opening through thermal processing on a core material with a predetermined outer diameter. Alternatively, the inner diameter may be decreased by connecting another tubular member to the inside of the tip end of the cylindrical part at the terminal end opening side.

There is no particular limitation on the shapes of the engagement portions as far as they can lock the bar-like operative instruments. For example, the cross sections of the tubular members along the thickness may be formed in the shape of a circle, a partly chipped circle, or a circle with at least one inward projection.

The widths of the engagement portions in the cylindrical parts need to be smaller than the largest width of the bar-like operative instrument. From the viewpoint of providing sufficient viewing fields of the lacrimal endoscopes, the widths of the cylindrical parts at the engagement portions are preferably 0.5 to 0.90 mm, and more preferably 0.65 to 0.86 mm.

Each of the engagement portions is positioned in the vicinity of the terminal end opening at a predetermined distance from the terminal end opening. The predetermined distance is determined from the viewpoints of acting as stoppers for the lacrimal endoscopes and providing sufficient viewing fields of the lacrimal endoscopes. For example, from the viewpoint of providing sufficient viewing fields of the lacrimal endoscopes, the lenses at the tip ends of the lacrimal endoscopes are preferably positioned within 2 mm from the most terminal end portions of the tube openings. From the viewpoint of providing viewing fields of 70% or more of the lacrimal endoscopes, the lenses at the tip ends of the lacrimal endoscopes are preferably positioned within 1.5 mm and more preferably within 1 mm, from the most terminal end portions of the tube openings. Therefore, from the viewpoint of providing sufficient viewing fields of the lacrimal endoscopes, the predetermined distance is preferably within 2 mm, more preferably within 1.5 mm, and further preferably within 1 mm from the terminal end openings (most terminal ends of the openings).

The longitudinal lengths of the engagement portions in the cylindrical parts may be any length as far as the cylindrical parts allow locking of bar-like operative instruments such as lacrimal endoscopes and provide sufficient viewing fields of the lacrimal endoscopes. For example, the longitudinal lengths of the engagement portions may fall within a range of 0.3 to 2 mm.

In the embodiment illustrated in FIGS. 2 to 5, the terminal end openings 13a and 13b of the cylindrical parts 14a and 14b are provided with the engagement portions 18a and 18b extended to the insides of the cylindrical parts, which makes the luminal parts 17a and 17b smaller in width. This prevents the tip ends of the bar-like operative instruments from coming into abutment with the engagement portions 18a and 18b and projecting outward from the terminal end openings 13a and 13b. There is no particular limitation on the structure of the engagement portions 18a and 18b. As described above, the engagement portions 18a and 18b may be provided continuously along the inner peripheral surfaces of the cylindrical parts, or may be provided at predetermined intervals. In addition, there is no particular limitation on the positions of the engagement portions 18a and 18b along the longitudinal sides of the tubular members. However, the engagement portions 18a and 18b are preferably positioned so as not to block the viewing fields of the lacrimal endoscopes, and are preferably provided at the terminal end of the cylindrical part 14a as in the embodiment illustrated in FIG. 5(a). The longitudinal widths of the engagement portions 18a and 18b may be set as appropriate taking into account the viewing fields of the lacrimal endoscopes. In the embodiment, the engagement portions are structured to be projected toward the inside. Alternatively, the engagement portions may be structured in any other manner as far as they are reduced in width of the luminal parts to prevent the outward projection of the bar-like operative instruments. For example, the engagement portions may each have a tapered structure in which the widths of the luminal parts are gradually reduced near the terminal end openings of the cylindrical parts with increasing proximity to the terminal end portions.

There is no particular limitation on the positions of the openings 16a and 16b for bar-like operative instrument. Preferably, the openings 16a and 16b for bar-like operative instruments are formed at positions of ⅔ or less of the entire lengths of the tubular members 11a and 11b from the terminal end openings 13a and 13b. In addition, the openings 16a and 16b for bar-like operative instruments are preferably formed at positions of ⅕ or more of the entire lengths of the tubular members 11a and 11b from the terminal end openings 13a and 13b.

The arc-shaped parts 15a and 15b are extended from the end portions of the cylindrical parts 14a and 14b at the central member 12 side toward the central member 12. In this embodiment, the arc-shaped parts 15a and 15b have circular arc-shaped wall portions 19a and 19b on the cross-sections orthogonal to the longitudinal sides of the tubular members 11a and 11b (for example, refer to FIG. 5(b)). The circular arc-shaped wall portions 19a and 19b are continuously formed at the arc-shaped parts 15a and 15b over lengths (la and lb) of ⅓ or more and 9/10 or less of entire lengths La and Lb of the tubular members 11a and 11b (in this embodiment, la/La (and lb/Lb) are ¾). By forming the circular arc-shaped wall portions 19a and 19b continuously along the longitudinal sides, wall portions with long, continuous cutouts along the longitudinal sides of the tubular members 11a and 11b (arc-shaped parts 15a and 15b) are formed as illustrated in FIGS. 2, 3, and 5. In this embodiment, the continuous cutouts are formed continuously in a straight line parallel to the longitudinal sides. However, the present invention is not limited to this. Alternatively, the cutouts may be altered in shape as appropriate by changing central angles described later continuously along the longitudinal sides or changing the circumferential positions of the circular arcs continuously along the longitudinal sides. Although the circular arc-shaped wall portions are formed with the cutouts in this embodiment, the circular arc-shaped wall portions may be formed with incisions. In the case of forming the incisions, the both end portions of the circular arc-shaped wall portions on the cross sections orthogonal to the longitudinal sides are in contact with each other in a separable manner.

In this embodiment, the circular arc-shaped wall portions 19a and 19b are formed over the entire longitudinal lengths of the arc-shaped parts 15a and 15b (tubular members 11a and 11b), but the present invention is not limited to this. Alternatively, almost arc-shaped wall portions may be formed at any positions of the arc-shaped parts. However, when the tubular members of the lacrimal duct tube are to be inserted ahead of the bar-like operative instruments into the lacrimal duct and be slid along the bar-like operative instruments for opening an obstructed site, it is preferred that almost arc-shaped wall portions are formed over the entire lengths of the sliding portions. This makes it easier to move the entire tubular members relatively along the bar-like operative instruments and hold the end portions of the tubular members at the central member sides. It is possible to transfer the pressing force of the arc-shaped parts to the terminal ends of the cylindrical parts in a more efficient manner and further improve operability for the operator.

In this embodiment, the longitudinal central axis 21a of the cylindrical part 14a is coaxial with the longitudinal central axis 22a of the arc-shaped part 15a, and the shortest distance between the central axis 21a and the cylindrical part 14a is equal to the shortest distance between the central axis 22a and the arc-shaped part 15a (refer to FIG. 5(a)), but the present invention is not limited to this. The central axes may not be coaxial with each other and the shortest distances may not be equal to each other. However, from the viewpoint of easily causing the entire tubular members to move relatively along the bar-like operative instruments and transferring the pressing forces of the arc-shaped parts to the terminal ends of the cylindrical parts in a more efficient manner, it is preferred that the longitudinal central axis of the cylindrical part and the longitudinal central axis of the arc-shaped part are coaxial with each other and the shortest distance between the longitudinal central axis and the cylindrical part and the shortest distance between the longitudinal central axis and the arc-shaped part are equal to each other. Although not illustrated, in this embodiment, the relationship between the central axis of the cylindrical part 14b and the central axis of the arc-shaped part 15b is the same as that between the cylindrical part 14a and the arc-shaped part 15a.

According to the present invention, the longitudinal central axes of the cylindrical parts and the arc-shaped parts almost align with the longitudinal central axes of the bar-like operative instruments attached to the tubular members.

In this embodiment, the circular arc-shaped wall portions 19a and 19b are employed as almost arc-shaped wall portions. However, the present invention is not limited to this but any other almost arc-shaped wall portions are applicable.

With regard to the "almost arc-shaped wall portions" included in the arc-shaped parts of the tubular members used in the present invention, the term "almost arc-shaped" means that a curve line, a straight line, a polygonal line, or a combination thereof is generally bent backward on the whole. The "backward bent state" also includes the states in which the subject is bent in a nearly linear shape or it is bent to the degree that both terminal ends thereof are in contact with each other in a separable manner. As specific examples of the "almost backward bent state," the subject may be entirely bent in a circular arc shape, a horseshoe shape, an U shape, an angled-U shape, a V shape, a multiangular shape, or the like, but is not limited to them. The term "wall portion" refers to an entire portion on the cross section of a member constituting the tubular member, which is surrounded and closed by a portion in contact with the bar-like operative instrument inserted into the cylindrical part and a portion not in contact with the bar-like operative instrument inserted into the cylindrical part. In the wall portion, the wall surface near the bar-like operative instrument and the wall surface distant from the bar-like operative instrument may be different in shape as far as the wall portion is almost arc-shaped on the whole.

In this embodiment, the circular arc-shaped wall portions 19a and 19b are configured such that central angles αa with reference to central points 20a on the cross sections orthogonal to the longitudinal sides of the tubular members 11a and 11b are 270 degrees. However, the present invention is not limited to this but the central angles αa may be set as appropriate as far as the angles allow the sufficient lengths of the almost arc-shaped wall portions. However, from the viewpoint of transferring more efficiently the pressing forces of the arc-shaped parts to the terminal ends of the cylindrical parts when the tubular members are inserted into the lacrimal duct along the bar-like operative instruments, and further improving the operability for the operator, the central angle is preferably 180 degrees or more.

At each of the almost arc-shaped wall portions in the present invention, the central point on the cross section orthogonal to the longitudinal side of the arc-shaped part exists on the longitudinal central axis of the arc-shaped part as described above. The central angle with reference to the central point is formed between two straight lines linking the central point and the two ends of the almost arc-shaped wall portion (for example, refer to the angle with the reference sign αa in FIG. 5(b), for example).

When the cross section orthogonal to the longitudinal side of the arc-shaped part is a circular arc-shaped, the central angle can be calculated from the distance between the both ends of the circular arc (chord length) and the inner and outer diameters of the circular arc. When the cross section orthogonal to the longitudinal side of the arc-shaped part is not a circular arc-shaped, the central angle can be measured by specification of the position of the central point on the central axis of the bar-like operative instrument with the largest width allowing insertion into the cylindrical part and the positions of the both ends of the almost arc-shaped wall portion by the cross section orthogonal to the longitudinal side of the arc-shaped part.

According to the present invention, at each of the almost arc-shaped wall portions, the central angle with reference to the central point on the cross section orthogonal to the longitudinal side of the tubular member can be set freely along the longitudinal side of the tubular member. In the embodiment illustrated in FIGS. 2 to 5, each of the central angles is set uniform along the longitudinal side. Alternatively, each of the almost arc-shaped wall portions may be configured to have a portion with the smaller central angle at the opening for bar-like operative instrument side along the longitudinal side of the tubular member. For example, the present invention may be configured such that: (A) each of the central angles becomes gradually smaller (the cutout becomes gradually larger) from the central member side to the opening for bar-like operative instrument side of the arc-shaped part; (B) each of the central angles becomes gradually smaller (the cutout becomes gradually larger) from the central member side to the opening for bar-like operative instrument side of the arc-shaped part and the central angle becomes gradually larger (the cutout becomes gradually smaller) toward the opening for bar-like operative instrument side; and (C) in appropriate combination with the configurations (A) and (B), each of the central angles is uniform from the central member side to the opening for bar-like operative instrument side of the arc-shaped part. However, the present invention is not limited to them.

Although there is no particular limitation on the central angles of the arc-shaped parts on the central member sides, the central angles are preferably 270 degrees or more, more preferably 300 degrees or more, and further preferably 350 degrees or more. Accordingly, the cutouts become larger in the cylindrical parts near the openings for bar-like operative instrument to improve insertability of the bar-like operative instruments, and the portions of the arc-shaped parts covering the bar-like operative instruments on the central member sides become larger to allow the operator to easily hold the lacrimal duct tube with improvement in operability.

According to the present invention, there is no particular limitation on the shape of the end portions of the arc-shaped parts at the central member sides. Preferably, as in the embodiment illustrated in FIGS. 2 to 5, the terminal ends 23a and 23b of the end portions are orthogonal to the longitudinal sides of the arc-shaped parts 15a and 15b (tubular members 11a and 11b). For example, as illustrated in FIG. 5(a), an angle βa formed by the central axis 22a of the arc-shaped part 15a and the plane including the end portion 23a is preferably a right angle. Accordingly, when each of the bar-like operative instruments is held by a clamp or the like and is arranged at a desired position in the tubular member, the end surface of the clamp and the end portion 23a or 23b of the arc-shaped part 15a or 15b come into abutment with each other to realize reliable positioning.

According to the present invention, there is no particular limitation on the shape of the both end portions of the almost arc-shaped wall portions (for example, the portions with reference sings 24a and 24b in FIG. 2 or with reference sign 24a in FIG. 5(b)). Preferably, the both end portions of the almost arc-shaped wall portions are rounded (for example, refer to FIGS. 6(b) and 6(c) described later). This makes it possible to easily prevent the both end portions from coming into contact with each other to cause damage to the lacrimal duct inner wall at the time of insertion into the lacrimal duct.

According to the present invention, there is no particular limitation on the material for the tubular members. A single material or two or more kinds of different materials may be used. In the case of using two or more kinds of different materials, the materials are preferably different in Shore hardness. The plurality of materials different in Shore hardness may be arranged with differences in Shore hardness in at least one of the direction along the longitudinal side of the tubular member, the direction along the cross section orthogonal to the longitudinal side (thickness direction), and the direction along the circumferential side. The materials different in Shore hardness may include a single material or a mixture of a plurality of materials.

The Shore hardness here refers to hardness measured by the ASTM2240 method. Similarly, the magnitude of hardness of the lacrimal duct tube in the present invention is determined by Shore hardness.

When each of the tubular members is structured such that the materials different in Shore hardness are layered in the thickness direction, the material for the portion sliding over the bar-like operative instrument (that is, the portion nearest to the bar-like operative instrument) at the time of attachment of the bar-like operative instrument is preferably highest in Shore hardness. This improves a sliding property between the bar-like operative instrument and the tubular member. At that time, the Shore hardness is preferably 57D or more. More preferably, the Shore hardness is 70D or more from the viewpoint of favorable passage through a lesion, operability of the tube in the lacrimal duct, and manipulation of the endoscope.

The materials for the tubular members may be, for example, polyolefin resins such as high-density polyethylene, low-density polyethylene, and polypropylene, silicone resins, polyamide resins such as polyamide and polyamide elastomer, polyurethane resins such as polyurethane and polyurethane elastomer, isobutylene copolymers, and resin compounds including alloys of the former ones. However, the materials are not limited to them.

When each of the tubular members is structured such that the materials having differences in Shore hardness in the thickness direction are layered, the material for the portion sliding over the bar-like operative instrument is preferably an olefin resin, more preferably a polyethylene, and most preferably a high-density polyethylene. This is advantageous in increasing a sliding property between the bar-like operative instrument and the tubular member, improving the balance between flexibility and rigidity, and enhancing the ease of layering of the different materials.

According to the present invention, the layer structure preferably has at least one set of layers in which the material for the inner layer is higher in hardness (for example, the Shore hardness of the material is 57D or more) than the material for the outer layer. Accordingly, when the lacrimal duct tube is to be used with bar-like operative instruments such as lacrimal endoscope attached to the cylindrical parts, the terminal ends of the tubular members are smaller in diameter and higher in hardness, thereby enhancing the property of passing through the lesion. This makes it possible to provide the highly operable lacrimal duct tube with improved pushability and decreased friction with the bar-like operative instruments.

In the foregoing layer structure, in particular, the constitutional material for the portion sliding over the bar-like operative instrument (the portion constituting the innermost layer) is higher in hardness than the constitutional materials for the other layers, which enhances the property of passing through the lesion and decreases friction with the bar-like operative instrument.

According to the present invention, in the layer structure, the outermost resin portion of the tubular member is formed from a polyamide elastomer or a mixed material of polyurethane and styrene-isobutylene-styrene block copolymer (SIBS), which produces an advantage in that the outer layer of the tubular member can be formed from the material excellent in flexibility, processability, and biocompatibility.

In the case of using the resin formed from polyurethane and SIBS as described above, the hardness of the resin portion can be adjusted by changing the ratio between polyurethane and SIBS. For example, as the proportion of polyurethane is increased, the resin portion is made higher in hardness. From the viewpoint of flexibility, the ratio of polyurethane to SIBS is preferably 1/99 to 99/1. The resin portion may be formed only from polyurethane and SIBS or may contain a mixture of other resin components.

The polyurethane is preferably any of thermoplastic polyurethane resins such as "Miractran E385PNAT" produced by Nippon Miractran Co., Ltd. and "Tekotan TT1074A" produced by Noveon Inc., which are ether aromatic cyclic polyurethanes, or "Tecoflex EG100A" and "Tecoflex EG85A" produced by Noveon Inc., which are ether cycloaliphatic polyurethanes, or "Karubotan PC3575A" produced by Noveon Inc., which is a polycarbonate-based polyurethane.

The SIBS is more preferably "SIBSTAR102T" produced by Kaneka Corporation.

In the case of providing each of the tubular members with a layer structure, the layer of the portion sliding over the bar-like operative instrument may be thickest. This is advantageous in the case where the tubular members need to be high in rigidity. In this case, the thickness of the layer is preferably 40 to 80% and more preferably 65 to 75%, of the total thickness of all the layers, although depending on the number of the layers.

In the case of using two or more kinds of materials for the tubular members as described above, the plurality of materials may be arranged with variations in Shore hardness in at least one of the direction along the longitudinal side, the direction along the thickness, and the direction along the circumference of the tubular member.

In the case of providing each of the tubular members with a layer structure, the layer of the portion of the cylindrical part sliding over the bar-like operative instrument may have an incision to facilitate bending of the tubular member. By providing a spiral incision in particular, it is possible to increase the hardness of the layer of the portion of the cylindrical part sliding over the bar-like operative instrument, and improve the operability of the lacrimal endoscope and the flexibility of the tubular member in a balanced manner.

When each of the tubular members needs to be high in rigidity, the tubular member may be provided with a reinforcement member over a portion ranging from the portion of the arc-shaped part in the vicinity of the central member to the portion continued from the arc-shaped part to the cylindrical part. There is no particular limitation on the structure of the reinforcement member. For example, the reinforcement member may be a single or plural linear bodies extended along the longitudinal side, but is not limited to this (as an example, refer to FIG. 8 described later).

There is no particular limitation on the material for the reinforcement member as far as it can provide reinforcement. For example, the material for the reinforcement member may be a shape-memory alloy such as a titanium-nickel alloy or a metallic material such as a stainless steel, but is not limited to them.

To enhance the insertability of the lacrimal duct tube into the lacrimal duct, the outsides of the tubular members may be coated with a hydrophilic coating. The coating develops the lubricity of the lacrimal duct tube in contact with the blood to reduce resistance at the time of insertion of the tube. Although there is no particular limitation on the kind of the hydrophilic coating, the coating is preferably formed from a hydrophilic polymer such as poly(2-hydroxyethyl methacrylate), polyacrylamide, polyvinylpyrrolidone, polyethyleneglycol, or the like, or a blended material thereof.

The tubular members in the present invention can be fabricated by various methods depending on their structure and material to be used. For example, the tubular members may be fabricated such that cylindrical parts and arc-shaped parts are separately produced and then they are joined together by a conventionally known technique such as welding or adhesion, or such that cylindrical members are formed by extrusion molding, and then cutouts or incisions are formed in some of the wall portions of the cylindrical members so as to form almost arc-shaped wall portions, thereby producing cylindrical parts and arc-shaped parts, or such that desired cylindrical parts and arc-shaped parts are formed by injection molding or compression molding using appropriate metal molds, or in any other method.

The central member 12 is a member connecting single ends of the paired tubular members. There is no particular limitation on the structure of the central member. For example, the central member may be a cylindrical body, a solid rod (columnar body), or the like. The thickness of the central member is preferably smaller than the thickness of the tubular member (the largest width of the cross section orthogonal to the longitudinal side). This realizes more stable placement of the lacrimal duct tube and reduces the patient's uncomfortable feeling. The material for the central member may be the same as that for the tubular members.

The central member 12 and the pair of tubular members can be separately fabricated and joined together by a method such as welding or adhesion. Reducing the central portion of the cylindrical member in diameter by thermal stretching or the like provides the lacrimal duct tube with the pair of tubular members and the central member connecting the tubular members at their ends.

Hereinafter, another embodiment will be described with reference to the drawings.

FIG. 6 illustrates schematically another embodiment of a lacrimal duct tube according to the present invention, in which the almost arc-shaped wall portions of the arc-shaped parts have the foregoing configuration (B) and the both ends of the almost arc-shaped wall portions are rounded. This embodiment is almost the same in structure as the embodiment illustrated in FIGS. 2 to 5, except for differences in the layer structure of the tubular members and the configuration of the almost arc-shaped wall portions. In this embodiment, tubular members 31a and 31b include cylindrical parts 34a and 34b and arc-shaped parts 35a and 35b. The pair of tubular members 31a and 31b is connected by the central member 12. The cylindrical parts 34a and 34b have terminal end openings 33a and 33b and engagement portions 38a and 38b. A central axis of the cylindrical part and a central axis (41b) of the arc-shaped part are coaxial with each other. A central point (40b) of the arc-shaped wall portion exists on the central axis.

In a lacrimal duct tube 30 of the embodiment illustrated in FIG. 6(a), the almost arc-shaped wall portions of the tubular members 31a and 31b are circular arc-shaped wall portions 39a and 39b. The circular arc-shaped wall portions 39a and 39b are configured such that: the central angles become gradually smaller (the cutouts become gradually larger in width) from the end portions of the arc-shaped parts 35a and 35b on the central member 12 sides toward openings (36a and 36b) for bar-like operation instrument (the central angles αb are set at 355 to 350 degrees up to the position at a length of about 9/10 of the entire length); the decrease rate of the central angles are more higher toward the openings (36a and 36b) for bar-like operation instrument (the central angles αb are set at 350 to 180 degrees from the position at a length of about 9/10 of the entire length to the position at a length of about 8.5/10 of the entire length); and the central angles become gradually larger with further increasing proximity to the openings (36a and 36b) for bar-like operation instrument (the cutouts become gradually smaller in width) (the central angles αb are set at 180 to 360 degrees from the position at a length of about 8.5/10 of the entire length to the position at a length of about 9/10 of the entire length). That is, in the embodiment of FIG. 6, the arc-shaped parts 35a and 35b have elongated straight cutouts and almost circular or almost oval cutouts formed by the circular arc-shaped wall portions 19a and 19b.

In addition, as illustrated in FIGS. 6(b) and 6(c), both end portions 44b of the circular arc-shaped wall portion 39b are rounded. Although not illustrated, the circular arc-shaped wall portion 39a of the tubular member 31a is structured in the same manner. In this embodiment, the tubular member 31b has a three-layer structure. As described above, the portion sliding over the bar-like operation instrument (hereinafter, referred to as an inner layer 45b in close proximity to the bar-like operative instrument) is a layer formed from a material with the highest Shore hardness among the three layers. An intermediate layer 46b is provided on the outside of the inner layer 45b, and an outer layer 47b is provided on the outside of the intermediate layer 46b. The inner layer 45b is thickest among the three. Although not illustrated, the tubular member 31a has the same multi-layer structure.

FIG. 7 illustrates schematically another embodiment of a lacrimal duct tube according to the present invention, in which the tubular members have a multilayer structure, and the almost arc-shaped wall portions of the arc-shaped parts have the foregoing configuration (C), and the both ends of the almost arc-shaped wall portions are rounded. This embodiment is almost the same in structure as the embodiment illustrated in FIGS. 2 to 5, except for differences in the layer structure of the tubular members and the configuration of the almost arc-shaped wall portions. In this embodiment, tubular members 51a and 51b include cylindrical parts 54a and 54b and arc-shaped parts 55a and 55b, the pair of tubular members 51a and 51b is connected by the central member 12, and the tubular parts 54a and 54b have terminal end openings 53a and 53b and engagement portions 58a and 58b. A central axis of the cylindrical part is coaxial with a central axis (61b) of the arc-shaped part, and a central point (60b) of the arc-shaped wall portion exists on the central axis.

In a lacrimal duct tube 50 of the embodiment illustrated in FIG. 7(a), the almost arc-shaped wall portions of the tubular members 51a and 51b are circular arc-shaped wall portions 59a and 59b. The circular arc-shaped wall portions 59a and 59b are configured such that: the central angles are uniform (the cutouts are uniform in width) from the end portions of the arc-shaped parts 55a and 55b on the central member 12 sides toward openings for bar-like operation instrument (56a and 56b) (the central angles αb are set at 180 degrees up to the position at a length of about 2/3 of the entire length); and the central angles become gradually larger with further increasing proximity to the openings (56a and 56b) for bar-like operation instrument (the cutouts become gradually smaller in width) (the central angles αb are set at 180 to 360 degrees). That is, in the embodiment of FIG. 7, the arc-shaped parts 55a and 55b have elongated straight cutouts and almost semi-circular arc-shaped or almost semi-elliptic arc-shaped cutouts of the same width formed by the circular-arc shaped wall portions 59a and 59b.

In addition, as illustrated in FIG. 7(b), both end portions 64b of the circular arc-shaped wall portion 59b are rounded. Although not illustrated, the circular arc-shaped wall portion 59a of the tubular member 51a is structured in the same manner. In this embodiment, the tubular member 51b has a three-layer structure. As described above, the portion sliding over the bar-like operation instrument (hereinafter, referred to as an inner layer 65b in close proximity to the bar-like operative instrument) is a layer formed from a material with the highest Shore hardness among the three layers. An intermediate layer 66b is provided on the outside of the inner layer 65b, and an outer layer 67b is provided on the outside of the intermediate layer 66b. The inner layer 65b is thickest among the three. Although not illustrated, the tubular member 51a has the same multi-layer structure.

FIG. 8 illustrates schematically another embodiment of a lacrimal duct tube according to the present invention, in which the tubular members have a multilayer structure, and the almost arc-shaped wall portions of the arc-shaped parts have the foregoing configuration (C), and the both ends of the almost arc-shaped wall portions are rounded. This embodiment is almost the same in structure as the embodiment illustrated in FIGS. 2 to 5, except for differences in the layer structure of the tubular members and the configuration of the almost arc-shaped wall portions. In this embodiment, tubular members 71a and 71b include cylindrical parts 74a and 74b and arc-shaped parts 75a and 75b, the pair of tubular members 71a and 71b is connected by the central member 12, and the tubular parts 74a and 74b have terminal end openings 73a and 73b and engagement portions 78a and 78b. A central axis of the cylindrical part is coaxial with a central axis (81b) of the arc-shaped part, and a central point (80b) of the arc-shaped wall portion exists on the central axis.

In a lacrimal duct tube 70 of the embodiment illustrated in FIG. 8(a), the almost arc-shaped wall portions of the tubular members 71a and 71b are circular arc-shaped wall portions 79a and 79b. The circular arc-shaped wall portions 79a and 79b are configured such that: the central angles are uniform (the cutouts are uniform in width) from the end portions of the arc-shaped parts 75a and 75b on the central member 12 sides toward openings (76a and 76b) for bar-like operation instrument (the central angles αb are set at 270 degrees up to the position at a length of about ⅝ of the entire length); and the central angles become gradually larger with further increasing proximity to the openings (76a and 76b) for bar-like operation instrument (the cutouts become gradually smaller in width) (the central angles αb are set at 270 to 360 degrees). That is, in the embodiment of FIG. 8, the arc-shaped parts 75a and 75b have elongated straight cutouts and almost semi-circular arc-shaped or almost semi-elliptic arc-shaped cutouts of the same width formed by the circular-arc shaped wall portions 79a and 79b.

In addition, as illustrated in FIG. 8(b), both end portions 84b of the circular arc-shaped wall portion 79b are rounded. Although not illustrated, the circular arc-shaped wall portion 79a of the tubular member 71a is structured in the same manner. In this embodiment, the tubular member 71b has a three-layer structure, and has reinforcement members 89b provided inside of the portion sliding over the bar-like operative instrument (hereinafter, referred to as an inner layer 90b in close proximity to the bar-like operative instrument). As described above, the inner layer 90b is a layer formed from a material with the highest Shore hardness among the three layers. An intermediate layer 87b is provided on the outside of the inner layer 90b, and an outer layer 88b is provided on the outside of the intermediate layer 87b. The inner layer 90b is thickest among the three. The inner layer 90b is formed as one layer by integrating a portion 85b in close proximity to the bar-like operative instrument and a portion 86b in close proximity to the intermediate layer. The reinforcement member 89b is arranged between the portion 85b and the portion 86b. This configuration of the inner layer 90b is preferable in the case where the reinforcement member 89b with the portions 85b and 86b of the same material is provided inside of the inner layer 90b. Alternatively, each of the portions 85b and 86b may be formed in two layers of different materials, thereby the inner layer 90b has a four-layer structure. In this case, the portion 85b is preferably highest in Shore hardness and thickest among the four layers. Although not illustrated, the tubular member 71a has the same multilayer structure as described above.

There is no particular limitation on bar-like operative instruments used in the present invention. The bar-like operative instruments may be operative bars (bougies), lacrimal endoscopes, or the like, for example.

Hereinafter, a method for using a lacrimal duct tube according to the present invention will be briefly described.

As illustrated in FIG. 4, the bar-like operative instruments 9a and 9b are attached to the lacrimal duct tube 10 illustrated in FIGS. 2 and 3. Then, the tubular member 11a with the bar-like operative instrument 9a is inserted from the lower lacrimal punctum 2 into the lower lacrimal canaliculus 4, the common canaliculus 5, the lacrimal sac 6, and the nasolacrimal duct 7 to open an obstructed site 100 in the nasolacrimal duct 7 (refer to FIGS. 1 and 9). At that time, as necessary, the tubular member 11a may be slid over the bar-like operative instrument 9a to penetrate the obstructed site 100 by the tip of the tubular member 11a (cylindrical part 14a). The bar-like operative instrument 9a may be a bougie or a lacrimal endoscope.

Next, as illustrated in FIG. 9, while the one tubular member 11a is inserted in the lacrimal duct, the other tubular member 11b with the bar-like operative instrument 9b is inserted from the upper lacrimal punctum 1 into the upper lacrimal canaliculus 3. The arc-shaped part 15b of the tubular member 11b has the circular arc-shaped wall portion 19b which allows the arc-shaped part 15b to be freely bent without not following the bar-like operative instrument 9b (refer to FIG. 9). Accordingly, even when the entire length of the lacrimal duct tube is short to the degree that does not need to be cut after placement in the lacrimal duct, the terminal end of the tubular member 11b can be arranged in the upper lacrimal punctum 1. After the tubular member 11b is inserted from the upper lacrimal punctum 1 into the upper lacrimal canaliculus 3, the circular arc-shaped wall portion 19b can be inserted along with the bar-like operative instrument 9b until reaching the obstructed site 100. As in the case of the tubular member 11a, as necessary, the tubular member 11b can be slid over the bar-like operative instrument 9b to penetrate the obstructed site 100 by the tip end of the tubular member 11b (the cylindrical part 14b).

In addition, as illustrated in FIG. 10, the total width of the cylindrical part 14b into which the bar-like operative instrument 9b is inserted and the bar-like operative instrument 9b is the same as width h1 of the cylindrical part 14b of the lacrimal duct tube 10 (refer to FIG. 10(b)). Meanwhile, at the side near the central member 12 across the opening 16b for bar-like operative instrument, the cylindrical part 14b is arranged, unlike in a conventional lacrimal duct tube (refer to FIG. 11), such that, when the bar-like operative instrument 9b is overlapped on the arc-shaped part 15b of the lacrimal duct tube 10, the circular-arc shaped wall portion 19b of the arc-shaped part 15b is incorporated into the side wall of the bar-like operative instrument 9b (the bar-like operative instrument 9b is inserted into the arc-shaped part 15b). Accordingly, the total width of the bar-like operative instrument 9b and the arc-shaped part 15b is a width h2 as a sum of thicknesses of the bar-like operative instrument 9b and the circular arc-shaped wall portion (refer to FIG. 10(c)), and the width h2 is smaller than the width h1 in the example of FIG. 10. Therefore, unlike in a conventional lacrimal duct tube, it is possible to easily insert the lacrimal duct tube 10 ahead of the opening 16b for bar-like operative instrument into the lacrimal duct, thereby reducing a burden on the patent. Since there is no edge of the opening on the central member 12 side of the opening 16b for bar-like operative instrument unlike in the conventional case (refer to the opening with reference sign 104 in FIG. 11), it is possible to easily operate the bar-like operative instrument 9b without hindrance to the longitudinal movement of the bar-like operative instrument 9b.

EXAMPLES

Example 1

Three-layer tubes with an outer diameter of 1.42 mm and an inner diameter of 0.96 mm were fabricated by multi-layer extrusion using an extruder, each of the tubes being configured to include: an inner layer with a cross-section thickness of 0.150 mm that was composed of a high-density polyethylene with a Shore hardness of 72D (HB530 produced by Japan Polyethylene Corporation); an intermediate layer with a cross-section thickness of 0.010 mm that was composed of a low-density polyethylene with a Shore hardness of 50D (PX3080 produced by Equistar Chemicals); and an outer layer with a cross-section thickness of 0.070 mm that was composed of a mixture (with a Shore hardness of 30D) of a polyurethane with a Shore hardness of 30D (Tecoflex EG85A produced by Noveon Inc.) and SIBS (SIBSTAR 102T produced by Kaneka Corporation).

A central member with an entire length of 25 mm was produced by molding a circular column-shaped member with an outer diameter of 0.70 mm using an extruder from a mixture of a polyurethane with a Share hardness of 30D (Tecoflex EG85A produced by Noveon Inc.) and SIBS (SIBSTAR 102T produced by Kaneka Corporation).

Each of the three-layer tubes with an entire length of 44 mm was cut in the side surface from the position at 11 mm from the tip end to form a cutout in the side surface such that the central angle on the cross section of the cutout orthogonal to the longitudinal side of the tube was 270 degrees, thereby to produce a cylindrical part and an arc-shaped part. The cutout constitutes the arc-shaped part with a circular arc-shaped wall portion. The corners on the both ends of the circular arc-shaped wall portion were entirely rounded along the longitudinal side by a metal trowel to form the tubular member.

The central member was arranged between the end portions of the thus fabricated pair of tubular members on the cutout sides. Then, the outer layer portions of the tubular members and the end portions of the central member were welded. After that, the terminal ends of the tubular members were reduced in inner diameter to 0.86 mm to form engagement portions, thereby manufacturing a lacrimal duct tube as generally illustrated in FIG. 3.

Example 2

As in the example 1, three-layer tubes were molded by multilayer extrusion using an extruder.

As in the example 1, a central member with an entire length of 25 mm was fabricated.

Each of the three-layer tubes with an entire length of 45 mm was cut in the side surface from the position at 30 mm from the tip end to form a cutout in the side surface such that the central angle on the cross section of the cutout orthogonal to the longitudinal side of the tube was 180 degrees. Then, as in the example 1, the corners on the both ends of the circular arc-shaped wall portion were rounded to form the tubular member.

The central member was arranged between the end portions of the thus fabricated pair of tubular members on the cutout sides. Then, the outer layer portions of the tubular members and the end portions of the central member were welded. After that, the terminal ends of the tubular members were reduced in inner diameter to 0.86 mm to form engagement portions, thereby manufacturing a lacrimal duct tube as generally illustrated in FIG. 7.

Example 3

As in the example 1, three-layer tubes were molded by multilayer extrusion using an extruder.

As in the example 1, a central member with an entire length of 25 mm was fabricated.

Each of the three-layer tubes with an entire length of 45 mm was cut in the side surface from the position at 4.5 mm from the tip end to form a cutout in a circle with a diameter of about 0.8 mm in the side surface such that the central angle on the cross section of the cutout orthogonal to the longitudinal side of the tube was 350 degrees. Then, as in the example 1, the corners on the both ends of the circular arc-shaped wall portion were rounded to form the tubular member.

The central member was arranged between the end portions of the thus fabricated pair of tubular members on the cutout sides. Then, the outer layer portions of the tubular members and the end portions of the central member were welded. After that, the terminal ends of the tubular members were reduced in inner diameter to 0.86 mm to form engagement portions, thereby manufacturing a lacrimal duct tube as generally illustrated in FIG. 6 (except for the shape of the cutout).

Example 4

As in the example 1, three-layer tubes were molded by multilayer extrusion using an extruder.

A tube with an outer diameter of 1.05 mm and an inner diameter of 0.95 mm was molded by an extruder from a high-density polyethylene with a Shore hardness of 72D (HB530 produced by Japan Polyethylene Corporation).

As in the example 1, a central member with an entire length of 25 mm was fabricated.

A Teflon-coated stainless steel mandrel (with an outer diameter of 0.94 mm) was passed through the high-density polyethylene tube with an entire length of about 60 mm. Then, a stainless steel reinforcement member with a cross section height of 0.10 mm, a width of 0.35 mm, and a length of 35 mm was made along the outer wall of the high-density polyethylene tube in the middle and its neighborhood into which the mandrel was inserted (such that the middle and its neighborhood of the 60-mm long high-density polyethylene tube and the middle and its neighborhood of the 35-mm long stainless steel reinforcement member were aligned with each other, for example, so that the stainless steel reinforcement member did not protrude from the both ends of the high-density polyethylene tube). The foregoing three-layer tube was extended and placed on the tube and the reinforcement member, and then these components were thermally welded while the outside was pressed by a shrink tube. Then, the mandrel was removed to produce a tube composed of three layers: the inner layer of high-density polyethylene in which a high-density polyethylene tube and a high-density polyethylene of an inner layer in the three-layer tube was integrated; the intermediate layer of a low-density polyethylene; and the outer layer of a mixture of polyurethane and SIBS, in which the inner layer was thickest and the stainless steel reinforcement member was arranged inside of the inner layer.

The tube was cut at one end at a position of 5 mm from the stainless steel reinforcement member, the cut end was set as a tip end, and the other end of the same was cut at a position of 45 mm from the tip end.

Then, each of the tubes was cut in the side surface from the position at 20 mm from the tip end to form a cutout in the side surface such that the central angle on the cross section of the cutout orthogonal to the longitudinal side of the tube was 270 degrees. Then, as in the example 1, the corners on the both ends of the circular arc-shaped wall portion were rounded to form the tubular member.

The central member was arranged between the end portions of the thus fabricated pair of tubular members on the cutout sides. Then, the outer layer portions of the tubular members and the end portions of the central member were welded. After that, the terminal ends of the tubular members were reduced in inner diameter to 0.86 mm to form engagement portions, thereby manufacturing a lacrimal duct tube as generally illustrated in FIG. 8.

Example 5

As in the example 1, three-layer tubes were molded by multilayer extrusion using an extruder.

A high-density polyethylene tube (HB530 produced by Japan Polyethylene Corporation) was molded by an extruder as in the Example 4.

As in the example 1, a central member with an entire length of 25 mm was fabricated.

In the same manner as in the Example 4 except that a shape-memory alloy reinforcement member of a titanium-nickel alloy with a cross section height of 0.10 mm, a width of 0.35 mm, and a length of 35 mm was used, tubes with the shape-memory alloy reinforcement member therein were fabricated.

In the same manner as in the Example 4 except that the foregoing tubes were used, a lacrimal duct tube as generally illustrated in FIG. 8 was produced.

REFERENCE SIGNS LIST

1 Upper lacrimal punctum
2 Lower lacrimal punctum
3 Upper lacrimal canaliculus
4 Lower lacrimal canaliculus
5 Common canaliculus
6 Lacrimal sac
7 Nasolacrimal duct
8 Inferior nasal meatus
9a, 9b Bar-like operative instrument
10 Lacrimal duct tube
11a, 11b Tubular member
12 Central member
13a, 13b Terminal end opening
14a, 14b Cylindrical part
15a, 15b Arc-shaped part
16a, 16b Opening for bar-like operative instrument
17a, 17b Luminal part
18a, 18b Engagement portion
19a, 19b Circular arc-shaped wall portion
20a Central point
21a Central axis of cylindrical part along longitudinal side
22a Central axis of arc-shaped part along longitudinal side
23a, 23b Terminal end
24a, 24b End portion of almost arc-shaped wall portion

The invention claimed is:

1. A lacrimal duct tube slidable along a bar-like operative instrument, comprising:
a pair of tubular members each of which has a terminal end opening at one end; and
a central member that connects other ends of the tubular members, wherein
at least one of the tubular members includes: a cylindrical part that is extended from the terminal end opening to the central member side and has an opening for bar-like operative instrument at an end portion at the central member side; and a substantially arc-shaped part that is extended from the end portion of the cylindrical part at the central member side further to the central member side, and
the substantially arc-shaped part is formed contiguously over a length of ⅓ or more and 9/10 or less of an entire length of the tubular member.

2. The lacrimal duct tube according to claim 1, wherein a longitudinal central axis of the cylindrical part and a longitudinal central axis of the substantially arc-shaped part are arranged coaxially, and the shortest distance between the central axis of the cylindrical part and the cylindrical part and the shortest distance between the central axis of the substantially arc-shaped part and the substantially arc-shaped part are equal.

3. The lacrimal duct tube according to claim 1, wherein the substantially arc-shaped part is contiguously arranged such that a central angle with reference to a central point on the cross section orthogonal to a longitudinal side of the substantially arc-shaped part is 180 degrees or more.

4. The lacrimal duct tube according to claim 1, wherein the substantially arc-shaped part has a portion in which a central angle with reference to the central point on the cross section orthogonal to a longitudinal side of the substantially arc-shaped part is smaller at the opening for bar-like operative instrument side along the longitudinal side of the substantially arc-shaped part.

5. The lacrimal duct tube according to claim 1, wherein the cylindrical part is circular cylindrical in shape, and the substantially arc-shaped part is formed of a circular arc-shaped wall portion on the cross section orthogonal to a longitudinal side of the substantially arc-shaped part.

6. The lacrimal duct tube according to claim 1, wherein the opening for bar-like operative instrument is formed at a position of ⅔ or less of the entire length of the tubular member from the terminal end opening.

7. The lacrimal duct tube according to claim 1, wherein the substantially arc-shaped part is rounded at both end portions of the cross section orthogonal to a longitudinal side of the tubular member.

8. The lacrimal duct tube according to claim 1, wherein the terminal end of the substantially arc-shaped part at the central member side has an end portion orthogonal to a longitudinal side of the substantially arc-shaped part.

9. The lacrimal duct tube according to claim 1, wherein the tubular member is composed of a plurality of materials different in Shore hardness, and the material for a portion of the tubular member sliding over the bar-like operative instrument is highest in Shore hardness.

10. The lacrimal duct tube according to claim 9, wherein the material for the portion sliding over the bar-like operative instrument is an olefin resin.

11. The lacrimal duct tube according to claim 9 or 10, wherein
the tubular member has a multilayer structure, and
of the multilayer structure, a layer constituting the portion sliding over the bar-like operative instrument is thickest.

12. The lacrimal duct tube according to claim 1, wherein a reinforcement member is arranged from a portion of the substantially arc-shaped part in the vicinity of the central member to a portion continued between the substantially arc-shaped part and the cylindrical part.

13. The lacrimal duct tube according to claim 12, wherein the reinforcement member is a stainless steel or a shape-memory alloy.

* * * * *